(12) United States Patent
French et al.

(10) Patent No.: US 9,078,598 B2
(45) Date of Patent: Jul. 14, 2015

(54) COGNITIVE FUNCTION EVALUATION AND REHABILITATION METHODS AND SYSTEMS

(71) Applicants: Barry J. French, Bay Village, OH (US); Neall M. French, Independence, OH (US)

(72) Inventors: Barry J. French, Bay Village, OH (US); Neall M. French, Independence, OH (US)

( * ) Notice: Subject to any disclaimer, the term of this patent is extended or adjusted under 35 U.S.C. 154(b) by 0 days.

(21) Appl. No.: 13/866,137

(22) Filed: Apr. 19, 2013

(65) Prior Publication Data

US 2014/0142439 A1 May 22, 2014

Related U.S. Application Data

(60) Provisional application No. 61/635,318, filed on Apr. 19, 2012.

(51) Int. Cl.
*A61B 5/11* (2006.01)

(52) U.S. Cl.
CPC *A61B 5/11* (2013.01); *A61B 5/1124* (2013.01)

(58) Field of Classification Search
CPC ...... A61B 5/11; A61B 5/1124; A61B 5/4088; A61N 1/36082
USPC ................................ 600/587, 595
See application file for complete search history.

(56) References Cited

U.S. PATENT DOCUMENTS

| 4,761,005 | A | 8/1988 | French et al. |
| 4,824,107 | A | 4/1989 | French |
| 4,883,271 | A | 11/1989 | French |
| 5,099,702 | A | 3/1992 | French |
| 5,249,967 | A | 10/1993 | O'Leary et al. |
| 5,469,740 | A | 11/1995 | French et al. |
| 5,524,637 | A | 6/1996 | Erickson |
| 6,073,489 | A | 6/2000 | French et al. |

(Continued)

FOREIGN PATENT DOCUMENTS

| EP | 0590101 A1 | 4/1994 |
| WO | 2004008427 A1 | 1/2004 |

OTHER PUBLICATIONS

Leddy, John J., et al., "Reliability of a Graded Exercise Test for Assessing Recovery From Concussion", Clinical Journal of Sports Medicine, (Mar. 2011), vol. 21, No. 2, pp. 89-94.

(Continued)

*Primary Examiner* — Max Hindenburg
(74) *Attorney, Agent, or Firm* — Renner, Otto, Boisselle & Sklar, LLP

(57) ABSTRACT

A cognitive function evaluation method and system involves prompting a test subject (person) to engage in movement, such as whole-body movement, for example sports-specific movement, while tracking movement of the person. Data can be gathered from the tracking of the person's movement. This data can be compared with baseline data from an earlier test (or with data gathered from other subjects), to make a determination of cognitive function of the test subject, or to evaluate progress in rehabilitation and/or aid in making a determination whether a person is ready to resume specified activities, such as an athlete returning to a sport. Such a determination can be made under realistic activity-specific conditions (for example using increased metabolic rate and/or activity-specific movements that may test/challenge the test subjects cognition, vestibular, and/or visual performance/abilities), to allow a for determination of the person's cognitive function.

23 Claims, 3 Drawing Sheets

(56) References Cited

U.S. PATENT DOCUMENTS

| | | | |
|---|---|---|---|
| 6,098,458 A | 8/2000 | French et al. | |
| 6,308,565 B1 | 10/2001 | French et al. | |
| 6,430,997 B1 | 8/2002 | French et al. | |
| 6,602,210 B2 * | 8/2003 | Savet | 600/595 |
| 6,734,834 B1 | 5/2004 | Baram | |
| 6,749,432 B2 * | 6/2004 | French et al. | 434/247 |
| 6,765,726 B2 | 7/2004 | French et al. | |
| 6,876,496 B2 | 4/2005 | French et al. | |
| 7,038,855 B2 | 5/2006 | French et al. | |
| 7,359,121 B2 * | 4/2008 | French et al. | 359/630 |
| 7,602,301 B1 | 10/2009 | Stirling et al. | |
| 7,634,379 B2 | 12/2009 | Noble | |
| 7,771,320 B2 | 8/2010 | Riley et al. | |
| 7,782,358 B2 * | 8/2010 | Nieminen et al. | 348/77 |
| 7,791,808 B2 | 9/2010 | French et al. | |
| 7,864,168 B2 | 1/2011 | French | |
| 8,048,002 B2 * | 11/2011 | Ghajar | 600/558 |
| 8,165,844 B2 | 4/2012 | Luinge et al. | |
| 8,342,978 B2 * | 1/2013 | Tamura | 473/212 |
| 8,503,086 B2 | 8/2013 | French et al. | |
| 8,529,448 B2 * | 9/2013 | McNair | 600/301 |
| 8,568,311 B2 * | 10/2013 | LaPlaca et al. | 600/301 |
| 8,671,784 B2 * | 3/2014 | Nishibayashi | 73/865.4 |
| 8,679,037 B2 * | 3/2014 | Sarig-Bahat | 600/595 |
| 2001/0015123 A1 | 8/2001 | Nishitani et al. | |
| 2006/0073449 A1 | 4/2006 | Kumar et al. | |
| 2008/0090703 A1 | 4/2008 | Rosenberg | |
| 2009/0270743 A1 | 10/2009 | Dugan et al. | |
| 2010/0103196 A1 | 4/2010 | Kumar et al. | |
| 2011/0270135 A1 | 11/2011 | Dooley et al. | |
| 2014/0134584 A1 | 5/2014 | French | |

OTHER PUBLICATIONS

Johnson, Philip et al., "Effect of Mild Brain Injury on an Instrumented Agility Task", Clinical Journal of Sports Medicine, (2002), vol. 12, No. 1, pp. 12-17.

* cited by examiner

COGNITIVE FUNCTION EVALUATION AND REHABILITATION METHODS AND SYSTEMS Priority is claimed under 35 USC 119 to U.S. Provisional Application 61/635,618, filed Apr. 19, 2012, which is incorporated by reference in its entirety.

BACKGROUND OF THE INVENTION

1. Field of the Invention

The invention is in the cognitive function evaluation devices and methods.

2. Description of the Related Art

Concussion, also known as mild traumatic brain injury (MTBI), has recently become widely recognized as a significant cause of disability in athletes. The currently accepted definition of concussion, that this injury represents a functional more than structure disorder, alludes to the fact that concussed athletes suffer from symptoms referable to disruptions in multiple physiologic systems, resulting in a diminution of overall physical performance. Studies show that sending an athlete back into action before the concussion or other neurological injury has healed may lead to further concussions in the short term, which may lead to permanent neurological defects in the long term.

In addition to decrements in cognition, vestibular and visual performance have been shown to be negatively effected by concussion. Additionally, it is well known that the increased metabolic demands associated with physical activity typically exacerbate these symptoms. In light of these facts, it would appear logical that in order to accurately evaluate and rehabilitate an athlete who has experienced a concussion that a comprehensive approach be utilized, one that addresses all aspects of the problem.

One tool utilized for the assessment of the ability of the athlete to return to play following concussion is IMPACT, a commercially available product that is categorized as a computer-based neurocognitive examination. There is an abundance of peer reviewed literature supporting its use in this capacity. The athlete is determined to have "recovered sufficiently" from his concussion once his IMPACT scores return to baseline or above. Current tests employed to assess the concussed athlete's ability to return to play (such as IMPACT) measure isolated capabilities. Such isolated testing does not accurately evaluate the athlete.

While IMPACT has been validated as a useful tool to determine restoration of baseline cognitive function following concussion, it does not adequately address the other physiologic system problems associated with concussion. Also, the test is taken in a sedentary state in which the athlete is able to focus all of their attentional resources to the test and as such the contribution of increased metabolic activity is not evaluated. Nor is the athlete's physical and/or physiological performance capabilities evaluated.

As discussed, tests such as IMPACT are neurocognitive tests for concussion recovery assessment measuring the speed and accuracy of tests of attention, speed, learning and working memory while the athlete is sedentary. Such tests are limited to the measurement of isolated capacities.

It is well accepted that movement defines functional capability. Orthopedic injuries affect the ability to react and move, as do brain injuries that impede the neurological system from properly signaling the musculoskeletal system. Measurement of the fundamental components of movement allows the clinician, trainer or coach to view disability and capability as a continuum of the capacity for movement.

The neuro-physical testing performed on static balance testing devices are limited to assessing aspects of the athlete's visual, vestibular or somatosensory systems that the athlete may rely on to maintain balance. The athlete typically remains stationary, i.e. the feet remain essentially in a fixed position. In summary, the perceived deficits of known concussion assessment devices include: 1) the inability to elevate the athlete's metabolic rate, as measured by heart rate, to levels consistent with game play; 2) they do not measure the athlete's reaction time to spontaneous (unplanned) stimuli that prompt sport-relevant movement responses, which are defined as multi-vector (3-dimensional) movement comprising distances approximating those of game play; and 3) they do not challenge the athlete's vision and vestibular system in a sport-relevant manner; prompting from the athlete 360 degree movements, i.e. the lateral, linear, vertical and rotational (turning) movements inherent in most sports.

In view of the above defects with current methods and systems, improvements in evaluation systems and methods would be desirable.

SUMMARY OF THE INVENTION

According to aspects of the invention, a method of evaluating cognitive function of a person includes: prompting the person to engage in full-body motion; tracking movement of the person while the person is engaging in the full-body motion, while gathering data regarding the movement of the person; and evaluating data obtained in the tracking movement. The method may optionally include one or more of the following features: the evaluating data includes comparing the data obtained in the tracking movement with data from a baseline evaluation; the evaluating data includes comparing the data obtained in the tracking movement with previously-collected data; the previously-collected data includes data from a baseline evaluation; the previously-collected data includes data from tracking movement of other persons; the prompting includes prompting the person to move in a sports-related way; the tracking movement includes tracking movement in three dimensions; the comparing data includes determining whether the person has a cognitive impairment; the comparing data includes determining whether the person is suffering from concussion symptoms; the comparing data includes determining whether the person is suffering from neurological disease symptoms; the prompting includes prompting the person to rotate the body of the person; the prompting includes prompting the person to engage in a test of reaction time; the comparing includes differentiating between changes in the data due to cognitive function changes, and changes in the data due to other causes that are not cognitive function changes; the comparing includes differentiating between changes in the data due to cognitive function changes, and changes in the data due to orthopedic function changes; the prompting includes elevating a heart rate of the person above a predetermined level during at least some of the gathering of the data during the tracking movement; the prompting includes elevating a heart rate of the person into a predetermined range during at least some of the gathering of the data during the tracking movement; the tracking includes tracking reaction time; the tracking reaction time includes tracking reaction time in various directions; the tracking includes reaction time, and/or movement speed/acceleration, and heart rate is also measured during the tracking; the comparing includes examining the reaction times for asymmetries with regard to direction; the evaluating includes isolating defects from orthopedic causes; and/or the evaluating includes isolating confounding factors.

According to other aspects of the invention, a method for cognitive function rehabilitation includes: prompting the person to engage in full-body motion; and tracking movement of the person while the person is engaging in the full-body motion, while gathering data regarding the movement of the person. The method may optionally include one or more of the following features: the method includes evaluating data obtained in the tracking movement; the prompting is controlled based at least in part upon the evaluating of the data; the prompting is controlled based at least in part upon cognitive health of the person; the prompting includes controlling one or more of rate of movement, distance of movement, and direction of movement, in response to cues; the prompting includes prompting the person to move in a sports-related way; the tracking includes reaction time, and/or movement speed/acceleration, and heart rate is also measured during the tracking; the gathering data includes gathering data regarding cognitive function symptoms in the person; the gathering data regarding cognitive function symptoms includes gathering data regarding the appearance of headaches in the person; the gathering data includes gathering data regarding the prompted motions that lead to the cognitive function symptoms; and/or the method includes determining rehabilitation status of the person from the data gathered during the tracking movement.

According to other aspects of the invention, a system for carrying out any of the methods of the previous paragraphs may include one or more of the following features: the system includes a camera; the camera has variable focus; the system includes a processor operatively coupled to the camera, or to another sensor, for tracking movement of the person; the system performs beaconless tracking of the person; the system includes a display for displaying to the person; the display includes a representation of a physical space in which movement of the person is tracked; and/or the display includes an avatar, movement of which corresponds to movement of the person in the physical space.

To the accomplishment of the foregoing and related ends, the invention comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

The annexed drawings, which are not necessarily to scale, show various aspects of the invention.

DETAILED DESCRIPTION

A cognitive function evaluation method and system involves prompting a test subject (person) to engage in movement, such as whole-body movement, for example sports-specific movement, while tracking movement of the person. Data can be gathered from the tracking of the person's movement. This data can be compared with baseline data from an earlier test (or with data gathered from other subjects), to make a determination of cognitive function of the test subject, or to evaluate progress in rehabilitation and/or aid in making a determination whether a person is ready to resume specified activities, such as an athlete returning to a sport. Such a determination can be made under realistic activity-specific conditions (for example using increased metabolic rate and/or activity-specific movements that may test/challenge the test subjects cognition, vestibular, and/or visual performance/abilities), to allow a for determination of the person's cognitive function. Specific movements that challenge visual/vestibular performance, such as turning movements or changes in elevation (such as upward and downward movements of the head) may be used to provide a better determination of cognitive function. Certain movements, such as reaction time tests for movements in various directions, may be used to help differentiate between performance reductions due to impair neurological function, and performance reductions for other reasons, such as orthopedic injuries, for example knee or ankle injuries.

A system for prompting user movement, tracking response, is the TRAZER system. An example of such a system is described in U.S. Pat. No. 7,359,121, which is incorporated herein by reference in its entirety. The TRAZER system is a physical activity system (a testing, training, recreational, and/or evaluation system) that includes a tracking system for determining changes in overall physical locations of a user (person or subject), and a processor or computer operatively coupled to the tracking system for updating a user virtual locations in a virtual space, a physical locations of the user. The TRAZER system may include a monitor or display, of any of various types, for providing information to a user of the system. The system may prompt movement in any of a variety of ways, provide feedback in a display, and gather data by tracking body movement in any of a variety of ways. Further details regarding the system, and the many body movements that may be prompted, and data that may be gathered, are described in the above patent.

Figure 1:
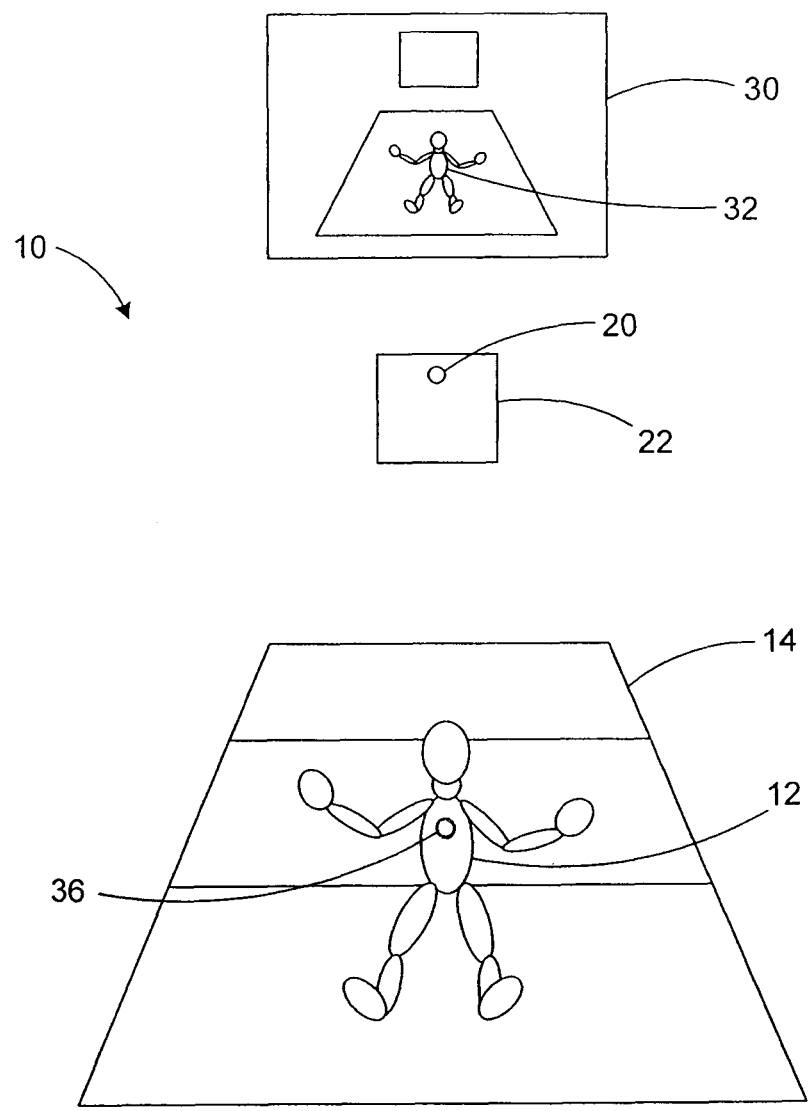
FIG. 1 is an oblique view of a system in accordance with an embodiment of the present invention.

FIG. 1 shows an example of a system 10, in some ways similar to the TRAZER system, which prompts full body movement of a person 12, in a physical space 14, which may or may not be visually delineated. Movement of the person 12 is detected and tracked by a camera or other sensor 20 in a base unit 22, which may include other components such as a processor, communication ability, data storage, etc. The camera or other sensor 20 may have an adjustable field for tracking the person 12, for example be adjustable to track in an area range from 36 square feet to 400 square feet. A display 26 is used to display a view 30 to the user 12, or to otherwise prompt full body motion to be tracked by the base unit 22. The view 30 may show an avatar 32 that represents movement of the user 12 in the physical space 14.

Heart rate may be measured by a commercially available wireless (telemetry) device 36 in essentially real-time. The wireless heart-rate monitor 36 may be worn on the person 12, with the monitor 36 in communication in real-time with the base unit 22.

The system 10 may also enable continuous, 360 degree body tracking of the athlete. A body-worn beacon, often used in prior systems, can often be dispensed with. Even without a beacon, the system 10 may be able to uniquely track certain types of movement that may be important for the sensitive and accurate assessment of a concussed athlete, or for another subject for neurological evaluation. The use of a 3D camera measuring depth eliminates the need for a body-worn beacon that previously precluded the reliable, continuous tracking of body movements such as body rotations and elevation changes. Body rotations refers to movements where the athlete (or person or subject) is turning away from the system 10 display by varying degrees. Such rotations may include full 360 degree turning.

Elevation changes are up or down changes in body locations. Prior patents involving the movement-tracking system (see the patent above, and other patents in its chain of priority) disclose the tracking of the user's CG (center-of-gravity), which was measurable in the some versions of the movement-tracking system by a body-worn beacon maintained line-of-sight with one or more sensors or other receiving elements. This required the athlete (user) to hold his or her torso in an erect posture—elevation changes were measured when the subject's legs either bent or the subject jumped. It has been found that vertical transgressions that involve the athlete dropping (approximately) his/her head below their heart level; which can occur when the athlete moves from a 3 or 4 point stance, reaches down to pick up a ball, etc., serves to more realistically challenge the athlete's sensory and vestibular systems.

The aforementioned types of movement add sophistication/realism to concussion or other neurological assessment. Some of these measurements, such as 360 degree body tracking of the subject, may also be accomplished in a system that utilizes one or more beacons on the subject.

A test protocol that assists in determining whether a measured degradation of global performance is caused, at least in part, from either a brain injury, orthopedic injury or maybe a contribution from both. Sensitivity and reliability of the assessment may benefit from the ability to determine whether an observed degradation of global performance is actually attributable to the effects of a brain injury.

A concussion may represent a diffused change in the metabolic state of the brain—that it is not a focal structural injury. As such, a global brain injury may result in degradation of global performance, as contrasted to a "focal" orthopedic injury or focal brain injury (a stroke) that results in vector-specific movement deficits.

There are, of course, many factors that may be attributable to differences between the athlete's preseason baseline test and testing employed post a concussion during season. Physical conditioning is just one potentially confounding factor.

By using the system 10 to analyze movement capabilities in each vector direction, it has been found that orthopedic injuries, especially lower extremity injuries, often produce movement deficits in defined movement vector. For example, moving off an injured right knee may inhibit reaction time and acceleration when the athlete is moving to the left, and may exhibit compromised deceleration capabilities when the athlete is moving to the right. Diminished reaction time as a result of an orthopedic injury may result from deterring pain, confidence and/or loss of proprioception; additionally acceleration/rate of force production deficits may also be observed.

An example test protocol begins with a stationary test to quantify magnitude of oscillations of the subject's body while the subject is standing upright. The subject is directed to stand still, and the sensor(s), such as the one or more cameras, are used to quantify the magnitude of oscillations of the subject's body. The stationary test may include tests of bilateral balance (subject standing with two feet shoulder's width apart, and with hands on hips), unilateral balance (subject standing on non-dominant foot, with free leg bent at a 90-degree angle, with hands on hips), and/or tandem balance (subject standing on non-dominant foot behind dominant foot, heal to toe). The standing/balance tests can be done on a firm surface and/or on a soft surface, such as on a foam cushion.

Figure 2:
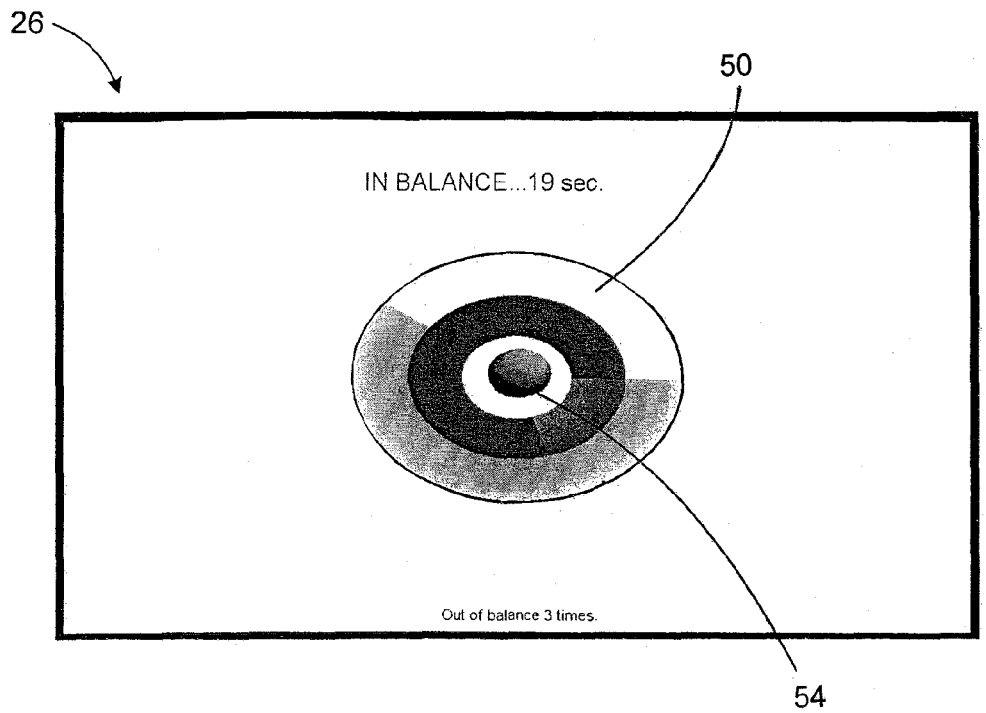
FIG. 2 is a screen shot showing a display used as part of a balance test.

The balance tests may involve feedback provided to the subject during the test. For example (with reference to FIG. 2), the subject, may be shown a target 50 on the display 26, with instructions to keep an indicator 54, corresponding to the user, in the center of the target 50. As the user moves (for example swaying while trying to keep his or her balance), the user indicator 54 moves on the display 26. Sufficient shifts in position of the user (e.g., shifts reaching certain boundaries within or surrounding the target 50) may be recorded as out-of-balance error events. In addition, out-of-balance distance may also be tracked and recorded.

Figure 3:
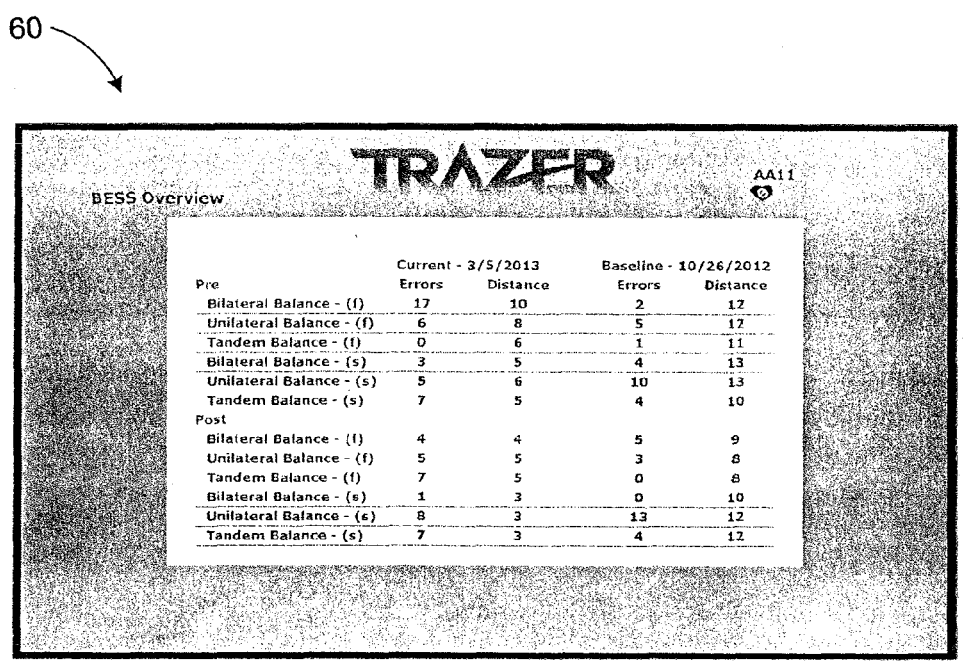
FIG. 3 is a table showing example balance test results.

The balance tests may be performed both before and after full-body motion of the user that raises the user's metabolic rate (including heart rate). Other ways may be possible to comingle balance test with directed movement exercises (such as directed three-dimensional movement). The results may be compared with baseline tests, with the results perhaps presented in a table, such as shown in FIG. 3. The table 60 shown in FIG. 3 is only one of a large variety of possible ways of presenting balance test results.

Figure 4:
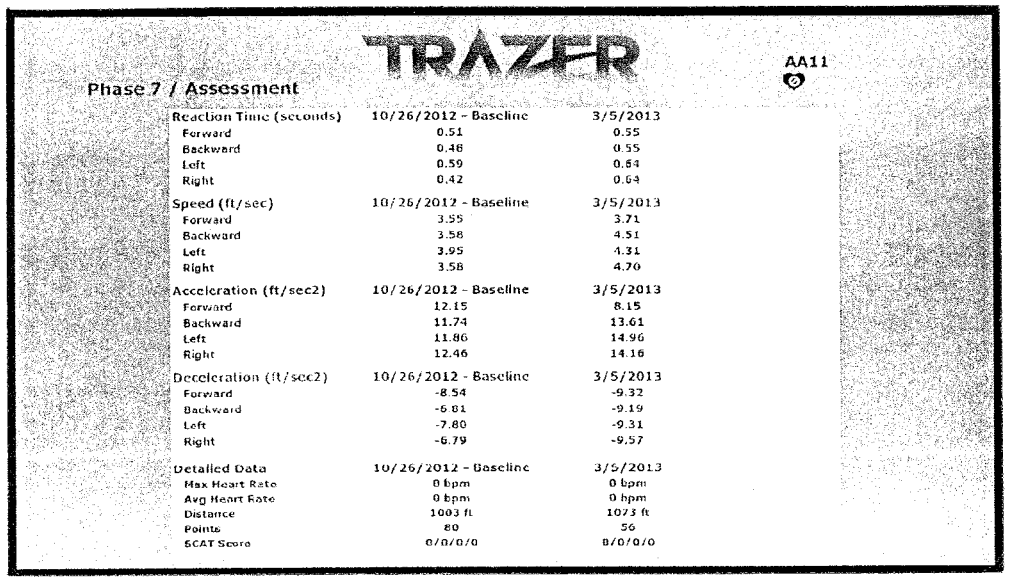
FIG. 4 is a table showing sample movement test results.

As described elsewhere herein, the movement prompted of the user may be task-specific movement, for example sports-specific movement, with the user prompted to make a variety of types of motions in a variety of directions. The results may be present in a table 80, such as is shown in FIG. 4. Parameters, such as reaction time, speed, acceleration, and deceleration, may be provided for different directions, such as forward and backward (e.g., toward and away from the display 26 (FIG. 1)), and left and right (e.g., opposite directions perpendicular to the display 26). In addition other data may be provided, for example regarding heart rate (or metabolic rate), distance traveled, and some sort of score. Baseline and current results may be provided for comparison and evaluation. Performance at baseline levels of performance (for example, within a margin or error or other difference), taking into account any orthopedic or other physical injuries, may be taken as an indication of a lack of cognitive or neurological deficit (either a lack of injury or an indication of recovery). A variety of criteria may be employed, including judgment of individuals on a case-by-case basis, taking into account an individual subject's health history.

Figure 5:
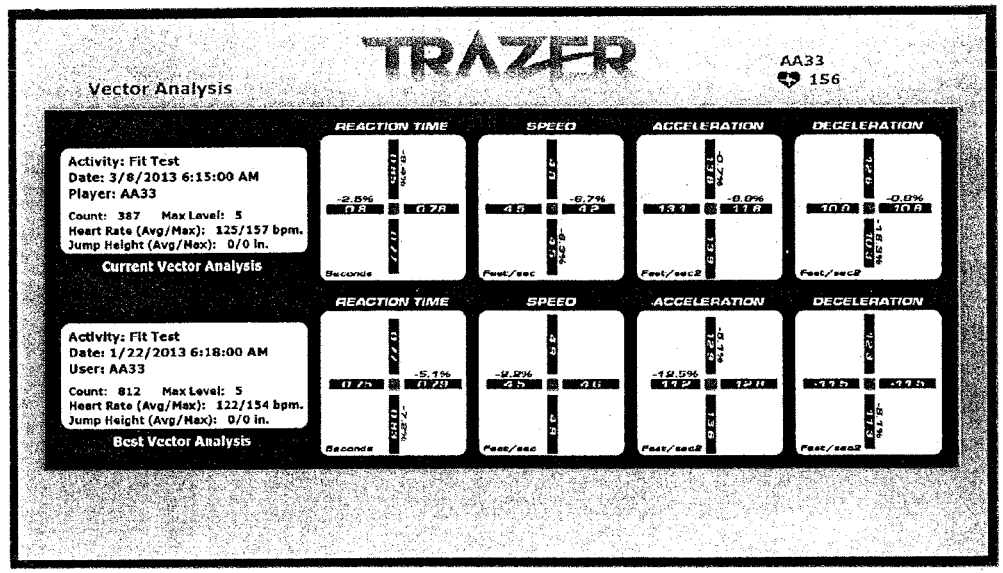
FIG. 5 is another table, showing sample movement test results in a different format.

FIG. 5 shows another presentation of results, a vector analysis presented graphically in a table 90. The table 90 provides a directional presentation of the forward-back and left-right differences in performance for a number of movement parameters, for both current and baseline tests (for example), providing easy comparison of results that may suggest trends.

Use of the system 10 to evaluate cognitive or neurological function contrasts with current tests employed to assess the concussed athlete's ability to return to play, which measure isolated capabilities. The system 10 has been employed to evaluate/assess the athlete's global athletic performance capabilities which may be compromised in the concussed athlete, or with those who have otherwise suffered cognitive or neurological deficits. The use of the system 10 in evaluation involves holistic approach to concussion assessment is in recognition that the status of the athlete (or other subject) cannot be understood solely in terms of its component parts.

Both orthopedic injuries, especially of the lower extremity, as well as brain injuries that act to impede the neurological system from properly signaling the musculoskeletal system, may affect the athlete's global athletic performance capabilities. The system 10 provides the interactive virtual environment and the measurement means to enable the clinician, trainer or coach to view disability and capability as a continuum of the capacity for movement. A concussion tends to degrade system-wide performance, in contrast to a lower extremity orthopedic injury that may act to degrade movement substantially in defined movement vectors.

In an improved method and system, such as described herein, for example using the system 10, a novel assessment protocol may be employed, using simulation to both measure global athletic performance and to assist the clinician in determining as to whether measured degradations (relative, for example, to a previously-performed baseline test) are resulting from a brain injury, orthopedic injury or both. Since returning a concussed athlete to play prematurely can result in catastrophic consequences, such information may assist the clinician in interpreting the available test data when making a return-to-play decision.

There are distinct advantages of assessing global performance in contrast to isolated capacities. The system and method described herein uniquely assesses the athlete's work capacity (the ability to sustain exercise while maintaining heart rate (or other indicators of metabolic rate) below a certain level), via the measurement of movement speed and heart rate, which is compared to the athlete's baseline assessment that was performed when the athlete was deemed healthy. Reaction time serves as a measure of sensory/cognitive prowess. The continuous measurement of the subject's movement speed and heart rate allows objective documenting work capacity, which can be compared to the subject's baseline (healthy) test results. Normative data can also used for comparison. A diminished capacity for work in a test after an event serves as a significant sign of neurological injury.

For example if movement speed during the assessment differs materially from the subject's baseline or from normative data, the clinician (test administrator) can then drill down by review of the subject's history (injuries, etc.), and examine pronounced vector differences in movement capabilities, to determine whether there might be an orthopedic reason for the slow-down. This would be evident through the comparison of vector differentials. However, changes in reaction time, heart rate and/or movement speed may also be used in assessing concussion or other neurological injury, either in conjunction with vector differentials, or as an alternative to vector differentials.

One goal in the present evaluation system and method is to assess the athlete's global performance capabilities that may be negatively affected as a direct result of a concussion. In addition the system and method may be capable of identifying potentially confounding factor(s) to that may contribute to diminished global performance. For example, a lower extremity orthopedic injury during season may impact the athlete's ability for movement that is obviously unrelated to diminished sensory/cognitive processes post concussion. Another possible confounding factor is that the athlete's present level of physical conditioning may differ from their preseason baseline due to either the rigors of the competitive season or as a direct result of the post concussion protocol that prescribes the athlete refrain from (minimally) vigorous exercise. To assist in identifying the impact of such confounding factors, the system and method provides means to assist in determining if the athlete's measured decline in work capacity may be related to a lower extremity orthopedic issue, or a more global decline as a result of a possible brain injury. It is possible that physical conditioning may have less impact on reaction time than the ability to generate high rates of force production (essentially acceleration). Therefore observing reaction time (collecting data on reaction time), and comparing reaction time versus a previous baseline (comparing data on reaction time versus baseline data on reaction time).

A brain injury may typically results in a universal (global) loss of the capacity for movement, rather than a "significant" deficit in a given movement vector. Accordingly, the ability to detect asymmetric movement patterns may serve to identify orthopedic issues that can negatively affect global performance. Such asymmetrical movement patterns may, for example, be the result of deterring pain, lack of confidence and/or proprioception in the injured limb as the subject attempts to accelerating off said limb. Both reaction time and acceleration specific to this vector may be diminished. The approach described herein may improve test sensitivity by the generation of movement-specific performance data to detect an "isolated" orthopedic deficit. Testing for symmetry of movement deficits could be performed for both baseline and post concussion return-to-play.

The system 10 described herein creates/replicates the physical demands of sport competition to measure "global athletic performance". In contrast to the assessment of isolated capacities, simulation acts to challenge the athlete's visual, cognitive, neuromuscular, and vestibular systems by eliciting 360 degree movement responses that act to elevate the athlete's metabolic rate to game levels while measuring reaction times to spontaneous cues, heart rate and multi-vector movement velocity. This measurement of work can be compared to previous baseline tests. Thus the system and method offer a novel global athletic performance assessment protocol for return to play decisions. Continuous measurement of heart rate and movement velocity in each vector direction gauges the athlete's work capacity as a measure of the athlete's compliance with the test protocol, which can be compared to baseline tests.

In the system 10, the athlete's perceptual (sensing) ability is not tested in isolation, but rather as the initial stage of a continuum of capabilities ranging from the ability to recognize and interpret sport-relevant visual information, to the ability to adeptly execute, when desired, in a kinematically correct manner. The athlete's visual and cognitive skills are challenged by sensing and responding to sports simulations that demand the athlete undertake the "correct" pursuit angle.

Injury to the vestibular system can directly create cognitive deficits and spatial navigation issues. The athlete responds to cues provided by the system 10 with rotations, translations and vertical changes of body position, each vector of movement may act somewhat differently on the vestibular system. The vestibular system contributes to balance and a sense of spatial orientation, essential components of effective athletic movement.

The approach described herein uniquely challenges the athlete's sensory and vestibular (balance) systems. With the system 10, the athlete responds with rotations, translations and vertical changes of body position to undertake the "correct" pursuit angle. This pursuit angle is known to TRAZER. Unlike static balance tests, aspects of depth perception, dynamic visual acuity, peripheral awareness and anticipation skills are assessed during realistic movement.

With an adjustable (modifiable) physical movement area, the assessment environment can uniquely replicate the movement patterns of game play, other athletic activity, or other task-specific activity. The assessment incorporates aspects of depth perception, dynamic visual acuity, peripheral awareness, anticipation skills, etc. Assessment of Dynamic Visual Acuity has been shown to be an excellent predictor of recovery from concussion. Unlike static tests, the systems and methods described herein uniquely assess aspects of Dynamic Visual Acuity by causing the athlete's head to be moved in space in a sport-specific manner.

Also material to test validity is the unpredictably of the stimuli delivered to the athlete over multiple tests. Randomizing software algorithms may be used to ensure that the athlete cannot correctly anticipate subsequent movement challenges.

Another advantage is that the interactive, game-like interface coupled to real time feedback also acts to improve the athlete's compliance with the testing or training protocol. Motivation is reported frequently as a recognized deficit of sedentary cognitive testing protocols.

Further, in contrast to specialized tests of cognition with a singular purpose, the system's versatility affords the clinician, trainer or coach many opportunities to collect baseline data for more accurate characterizations of the athlete's baseline global performance. For example, sports simulation provides unrivaled testing and training opportunities during the athlete's strength and conditioning and rehabilitation sessions. TRAZER thus serves as data collection, analysis and reporting system that detects movement (performance) abnormalities and weaknesses.

Many other variations are possible. The above system and steps may also be employed as part of a rehabilitation process, for example in rehabilitating an athlete from an injury such as a concussion. The system 10 may be used for controlled rehabilitation of an injured person, and for aiding in determining when the person is ready to resume specified activities, such as a team sport or other athletic activity. Comparisons can be made relative to a baseline (pre-injury) test, or alternatively relative to data from other persons, for example data from similar types of athletes, such as those with similar body types and/or skills.

Resting heart rate for a healthy young athlete may be 45-70 beats per minute (bpm), for example. During a sport and/or task the heart rate may raise considerably, for example a basketball player on a fast break may achieve a heart rate in excess of 150 to 180 bpm. When testing post concussion to compare to a baseline (or normative data), it is beneficial for the athlete to reach a heart rate commensurate to levels achieved in actual competition. Combining a system for prompting movement, with feedback concerning heart rate, allows this to be accomplished. The measurement of heart rate and movement speed may be used as indicators of the athlete's capacity for work. For example, assume an athlete's baseline test measured a maximum velocity of 6.2 ft/sec, maximum heart rate of 185 bpm, and average reaction time of 0.7 sec. If the athlete post concussion achieves these baseline levels without symptoms, it may be assumed that he or she is now "fit to play".

The system 10 and methods described above may be used for rehabilitation, such as for recovery from a concussion or other neurological injury. By controlling performance through use of prompts for user movement, and by measuring response through tracking, the progression of the rehabilitation process can be controlled. The system 10 (FIG. 1) allows the precise control of movement (e.g., the rate, distance and/or direction that the subject travels in response to the visual stimuli). Movement can be prompted over varying distances and directions to modulate the intensity of the exercise, for example to avoid reinjury by attempting overly intense exercise. Thus the resulting rehabilitation can follow a scripted, return-to-play exercise program for concussion that is based on the Zurich "Graduated Return to Play Protocol." Measurements during exercise can be invaluable for controlling the progression rate. Such measurements are compared to baseline (pre-injury) tests and/or to normative ranges. By using realtime measurements of fundamental performance and physiological factors, coupled with an interactive training environment, the system advantageously improves on current methods for Zurich Protocols that include rehabilitation stages progressing from light aerobic exercise to sport-specific (task-specific) exercise to non-contact training drills.

Some movement constructs have been discussed above in connection with cognitive or neurological testing and/or rehabilitation. A wide variety of other measurements or constructs may be utilized alternatively or in combination, including a measure of work performed by the player, a measure of the player's velocity, a measure of the player's power, a measure of the player's ability to maximize spatial differences over time between the player and a virtual protagonist, a time in compliance, a measure of the player's acceleration, a measure of the player's ability to rapidly change direction of movement, a measure of dynamic reaction time, a measure of elapsed time from presentation of a cue to the player's initial movement in response to the cue, a measure of direction of the initial movement relative to a desired response direction, a measure of cutting ability, a measure of phase lag time, a measure of first step quickness, a measure of jumping or bounding, a measure of cardio-respiratory status, and a measure of sports posture. Data can be obtained with regard to any or all of these parameters, as well as many others, and stored and evaluated in any of a variety of suitable ways, using any of a variety of suitable methods.

The system is described in terms of cognitive testing and evaluation in terms of brain injuries, for example concussions. Alternatively the system may be used for evaluation of other cognitive conditions, for example neurological diseases.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method of evaluating cognitive function of a person, the method comprising:
   prompting the person to engage in full-body multi-dimensional motion, with motions in a variety of directions, wherein the prompting includes prompting to cause an increase of metabolic rate of the person;
   tracking movement of the person in multiple dimensions while the person is engaging in the full-body motion, while gathering data regarding the movement of the person;
   measuring heart rate during the prompting and the tracking; and
   evaluating data obtained in the tracking movement and the measuring the heart rate, for heart rate responses to the elevated metabolic rate and/or for appearance of symptoms associated with cognitive impairment, to determine whether the person has a cognitive impairment.

2. The method of claim 1, wherein the evaluating data includes comparing the data obtained in the tracking movement with previously-collected data.

3. The method of claim 2, wherein the previously-collected data includes data from a baseline evaluation.

4. The method of claim 2, wherein the previously-collected data includes data from tracking movement of other persons.

5. The method of claim 1, wherein the comparing data includes determining whether the person is suffering from concussion symptoms.

6. The method of claim 1, wherein the comparing data includes determining whether the person is suffering from neurological disease symptoms.

7. The method of claim 2, wherein the comparing includes distinguishing between changes in the data due to cognitive function changes, and changes in the data due to other causes that are not cognitive function changes.

8. The method of claim 2, wherein the comparing includes distinguishing between changes in the data due to cognitive function changes, and changes in the data due to orthopedic function changes.

9. The method of claim 1, wherein the prompting includes prompting the person to move in a sports-related way.

10. The method of claim 1, wherein the prompting includes prompting the person to rotate the body of the person.

11. A method for cognitive function rehabilitation, the method comprising:
   prompting the person to engage in full-body motion, wherein the prompting includes prompting to cause an increase of heart rate of the person;
   tracking movement of the person while the person is engaging in the full-body motion, while gathering data regarding the movement of the person; and
   evaluating movement data obtained in the tracking movement;
   wherein the prompting includes controlling one or more of rate of movement, distance of movement, and direction of movement, in response to cues; and
   wherein the evaluating data includes determining a work capacity of the person to sustain exercise, from speed of the full-body motion obtained during the tracking.

12. The method of claim 11, wherein the prompting is controlled based at least in part upon the evaluating of the data.

13. The method of claim 11, wherein the prompting is controlled based at least in part upon cognitive health of the person.

14. The method of claim 11, wherein the prompting includes prompting the person to move in a sports-related way.

15. The method of claim 11, wherein the tracking includes reaction time, and/or movement speed/acceleration, and heart rate is also measured during the tracking.

16. The method of claim 1, wherein the prompting to cause the increase in the metabolic rate includes prompting to cause an increase of heart rate of the person to a level commensurate with a heart rate measured in a baseline test involving prompting the person to engage in full-body motion.

17. The method of claim 1,
   further comprising:
      before the prompting and the tracking, performing a first static balance test on the person, to quantify the magnitude of oscillations of the person, prior to the increase of the heart rate; and
      after the prompting and the tracking, performing a second static balance test on the person, to quantify the magnitude of oscillations of the person, while the heart rate is still increased;
   wherein the evaluating also includes using results of the balance tests as indicators of possible impairment of cognitive function.

18. The method of claim 17,
   wherein the prompting includes prompting the person to move in a sports-related way; and
   wherein the prompting includes prompting to cause the increase of heart rate of the person to a level commensurate with a sports-related activity simulated by the prompting.

19. The method of claim 8, wherein the distinguishing includes comparing movement deficits in different movement vectors, with cognitive function impairment indicated by generalized symmetric movement deficit in the different movement vectors, and with orthopedic impairment indicated by asymmetric movement deficit in the different movement vectors.

20. The method of claim 10, wherein the prompting to rotate the body includes prompting to rotate the body about 180 degrees of rotation.

21. The method of claim 1, wherein the prompting to cause an increase in heart rate includes prompting to cause an increase of heart rate of at least 150 beats per minute.

22. The method of claim 1, wherein the evaluating includes determining a work capacity of the person to sustain exercise, from speed of the full-body motion obtained during the tracking, and from the heart rate of the person measured during the measuring.

23. A method of evaluating cognitive function of a person, the method comprising:
   performing a first test, the first test including:
      prompting the person to engage in full-body multi-dimensional motion, with motions in a variety of directions, wherein the prompting includes prompting to cause an increase of metabolic rate of the person;
      tracking movement of the person in multiple dimensions while the person is engaging in the full-body motion, while gathering data regarding the movement of the person;
      measuring heart rate during the prompting and the tracking; and
      evaluating data obtained in the tracking movement and the measuring the heart rate, to determine the person's baseline work capacity to sustain exercise;
   subsequent to the at least the prompting, the tracking movement, and the measuring heart rate of the first test, performing a second test that also includes the prompting, the tracking movement, and the measuring heart rate, as well as determining an updated work capacity to sustain exercise from the tracking movement of the second test and the measuring the heart rate of the second test; and
   comparing the updated work capacity to sustain exercise with the baseline work capacity to sustain exercise.

* * * * *